United States Patent
Ali et al.

(10) Patent No.: US 9,120,094 B2
(45) Date of Patent: Sep. 1, 2015

(54) POLYMERIZATION OF BIS[3-(DIETHOXYPHOSPHORYL)PROPYL] DIALLYLAMMONIUM CHLORIDE

(71) Applicants: King Fahd University of Petroleum and Minerals, Dhahran (SA); King Abdulaziz City for Science and Technology, Riyadh (SA)

(72) Inventors: Shaikh Asrof Ali, Dhahran (SA); Shamsuddeen Abdullahi Haladu, Dhahran (SA); Hasan Ali Al-Muallem, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 79 days.

(21) Appl. No.: 14/139,041

(22) Filed: Dec. 23, 2013

(65) Prior Publication Data

US 2015/0174572 A1    Jun. 25, 2015

(51) Int. Cl.
*C08G 75/20* (2006.01)
*B01J 41/14* (2006.01)
*C07F 9/40* (2006.01)

(52) U.S. Cl.
CPC ............... *B01J 41/14* (2013.01); *C07F 9/4009* (2013.01)

(58) Field of Classification Search
CPC .................................. C02F 1/68; C08G 75/22
USPC .............................. 526/278; 521/38; 558/158
IPC .................................... C02F 1/68; C08G 75/22
See application file for complete search history.

(56) References Cited

U.S. PATENT DOCUMENTS

2014/0190895 A1 *   7/2014   Rahman et al. ............... 210/700

FOREIGN PATENT DOCUMENTS

| WO | WO 2005/117188 A1 | 12/2005 |
| WO | WO 2007/009917 A1 | 1/2007 |

OTHER PUBLICATIONS

U.S. Appl. No. 14/144,094, filed Dec. 30, 2013, Ali, et al.
U.S. Appl. No. 14/092,363, filed Nov. 27, 2013, Ali, et al.

* cited by examiner

*Primary Examiner* — Ling Choi
*Assistant Examiner* — Chun-Cheng Wang
(74) *Attorney, Agent, or Firm* — Oblon, McClelland, Maier & Neustadt, L.L.P.

(57) ABSTRACT

A symmetrically substituted cationic monomer and its corresponding cationic polyelectrolyte (CPE) (+) bearing two identical (diethoxyphosphoryl)propyl pendent groups on repeating pyrrolidinium units. Phosphonate ester hydrolysis in (CPE) (+) forms a pH-responsive cationic polyacid (CPA) (+). The (CPA) (+) is converted under pH-induced transformation into a polyzwitterion acid (±) (PZA) or a polyzwitterion/anion (±−) (PZAN) or a polyzwitterion/dianion (±=) (PZDAN) or a polyzwitterion/trianion (±≡) (PZTAN).

15 Claims, 7 Drawing Sheets

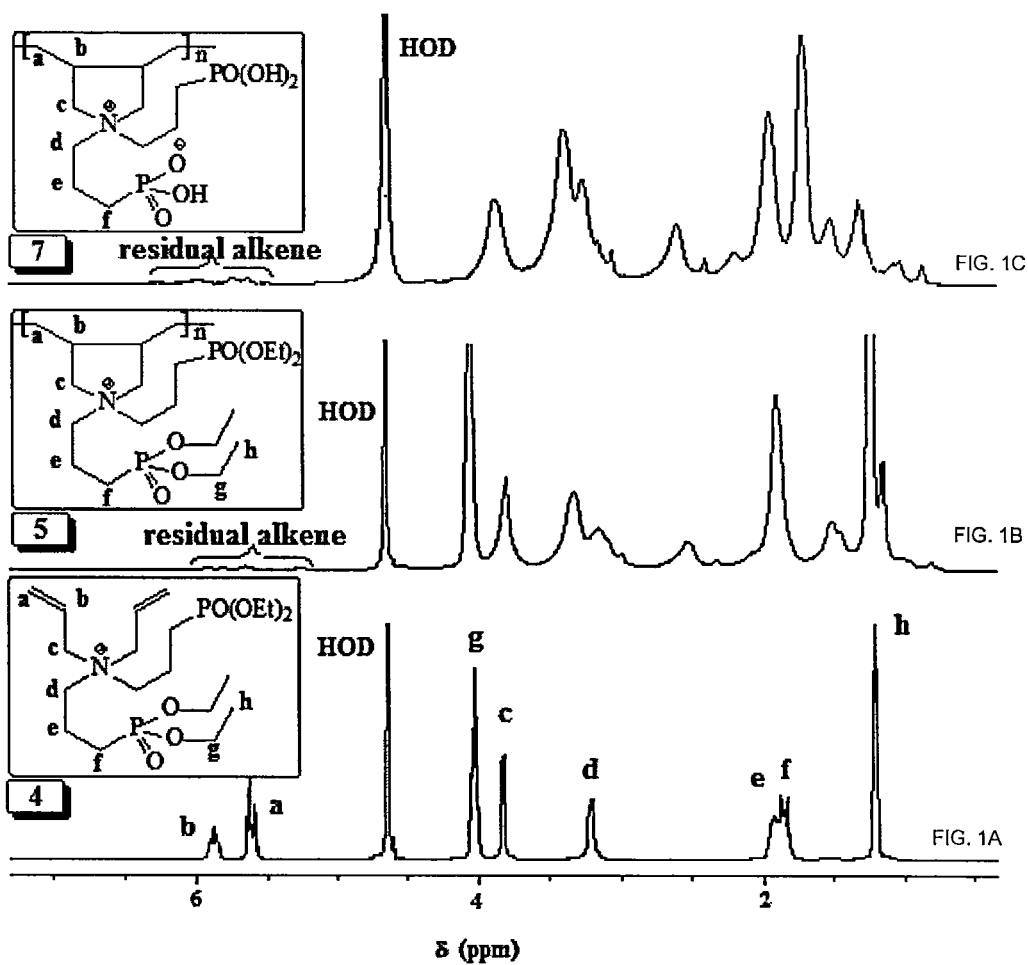

POLYMERIZATION OF BIS[3-(DIETHOXYPHOSPHORYL)PROPYL] DIALLYLAMMONIUM CHLORIDE

BACKGROUND OF THE INVENTION

1. Technical Field

The present invention relates to a symmetrically substituted cationic monomer, a cationic polyelectrolyte synthesized from the symmetrically substituted cationic monomer, a pH-responsive cationic polyacid synthesized from the cationic polyelectrolyte, a polyzwitterionic acid synthesized from the cationic polyacid, a polyzwitterion/anion and polyzwitterion/dianon synthesized from the polyzwitterionic acid, and the corresponding methods by which each compound and polymer is formed and use of the polyzwitterionic acid as an antiscalant.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Phosphorus, one of the essential elements required for life on earth, is observed in biology in the form of a phosphate or a pyrophosphate which is a required component of DNA, RNA, phospholipids and adenosine triphosphate (ATP). Phosphonates on the other hand are less common in nature (Horiguchi, M.; Kandatsu, M. *Nature* 1959, 184, 901; K. D. Demadis In Progress in Solid State Chemistry Research, Buckley, R. W. Ed.; 2007 Nova Science Publishers, Inc.; ISBN 1-60021-567-X; pp. 109-172—each incorporated herein by reference in its entirety); however, numerous synthetic organic phosphonates phosphonates have found widespread use in various industries (Ternan, N. G.; Mc Grath, J. W.; Mc Mullan, G.; Quinn, J. P. *World J. Microb. Biot.* 1998, 14, 635—incorporated herein by reference in its entirety). Phosphonates have been used to chelate divalent cations such as $Ca^{2+}$ and $Ba^{2+}$ ions (Nowack, B. *Water Res.* 2003, 37, 25331; Thatcher, G. R. J.; Campbell, A. S. *J. Org. Chem.* 1993, 58, 2272—each incorporated herein by reference in its entirety) in water softening, detergents, textile industry as well as to inhibit the deposition of scale. Polymers containing both amine and phosphonic acid groups are used as chelating resins for metal ions (Alexandratos, S. D.; Hong, M. J. *Sep. Sci. Technol.* 2002, 37, 2587; Eiffler, J.; Joeken, G.; Schneider, H. P., Invs; The Dow Chemical Co., U.S. Pat. No. 5,109,074, Apr. 28, 1992; Alfano, N. J.; Shenberger, D. M., Invs; Calgon Co., U.S. Pat. No. 5,454,954, Oct. 3, 1995; Sato, Y.; Murayama, K.; Nakai, Y., Invs; General Agency of Industrial Science and Technology, U.S. Pat. No. 5,212,207, May 18, 1993; Riedelsberger, K.; Jaeger, W. *Des. Mon. Polym.* 1998, 1, 387). Butler's cyclopolymerization protocol (Butler, G. B. Cyclopolymerization and Cyclocopolymerization; Marcel Dekker: New York, 1992; Kudaibergenov, S.; Jaeger, W.; Laschewsky, A. *Advances in Polymer Science* 2006, 201, 157; Singh, P. K.; Singh, V. K.; M. Singh, *e-Polymers* 2007, 030, 1; Jaeger, W.; Bohrisch, J.; Laschewsky, A. *Prog. Polym. Sci.* 2010, 35, 511—each incorporated herein by reference in its entirety) using diallylamine salts bearing aminomethylphosphonate motif has been utilized in the synthesis of cross-linked polyphosphonate resins which are found to be very effective in the removal of toxic metal ions (Al Hamouz O. C. S.; Ali, S. A. *Ind. Eng. Chem. Res.* 2012, 51, 14178; Al Hamouz, O. C. S.; Ali, S. A. *Sep. Purific. Technol.* 2012, 98, 94—each incorporated herein by reference in its entirety).

The area of applications also includes ion exchangers (Ortiz-Avila, C. Y.; Bhardwaj, C.; Clearfield, A. *Inorg. Chem.* 1994, 33, 2499—incorporated herein by reference in its entirety), nonlinear optics (Petruska, M. A.; Watson, B. C.; Meisel, M. W.; Talham, D. R. *Chem. Mater.* 2002, 14, 2011; Cao, G.; Hong, H. G.; Thompson, M. E. *Acc. Chem. Res.* 1992, 25, 420; Fu, R.; Zhang, H.; Wang, L.; Hu, S.; Li, Y.; Huang, X.; Wu, X. *Eur. J. Inorg. Chem.* 2005, 3211—each incorporated herein by reference in its entirety), catalysts (Benitez, I. O.; Bujoli, B.; Camus, L. J.; Lee, C. M.; Odobel, F. Talham, D. R. *J. Am. Chem. Soc.* 2002, 124, 4363—incorporated herein by reference in its entirety), and molecular sensors (Brousseau III, L. C.; Aurentz, D. J.; Benesi, A. J.; Mallouk, T. E. *Anal. Chem.* 1997, 69, 688—incorporated herein by reference in its entirety). A novel sulfonated poly (ether ether ketone)/phosphonated polysulfone polymer blends for proton conducting membranes was recently reported (Abu-Thabit, N. Y.; Ali, S. A.; Zaidi, S. M. J.; Mezghani, K. *J. mater. Res.* 2012, 27 1958—incorporated herein by reference in its entirety). Cyclopolymers bearing aminopropylphosphonate motif have been synthesized and evaluated as antiscalants (Kazi, I. W.; Rahman, F.; Ali, S. A. *Polym. Engg. Sci.*: DOI 10.1002/pen.23548; Ali, S. A.; Kazi, I. W.; Rahman F. *Polym. Int.* DOI 10.1002/pi.4539—each incorporated herein by reference in its entirety) and as a polymer component in the construction of aqueous two-phase systems (Al-Hamouz, O. C. S.; Ali, S. A. *J. Chem. Eng. Data* 2013, 58, 1407—incorporated herein by reference in its entirety). Some phosphonates are used as medicines: the antiretroviral drug Tenofovir is used in the treatment of viral diseases such as HIV and hepatitis B (De Clercq, E. *Annu. Rev. Pharmacol. Toxicol.* 2011, 51, 1. —incorporated herein by reference in its entirety). Aminophosphonic acids are structural analogues of amino acids and as such suitable for various biological applications (Kafarski, P.; Lejczak, B. *Phosphorus Sulfur Silicon* 1991, 63, 193—incorporated herein by reference in its entirety). Two recent reports describe the polymerizations of phosphonated-bis(methacrylamide)s for dental applications (Akgun, B.; Savci, E.; Avci, D. *J. Polym. Sci. Part A: Polym. Chem.* 2012, 50, 801; Bilgici, Z. S.; Ordu, O. D.; Isik, M.; Avci, D. *J. Polym. Sci. Part A: Polym. Chem.* 2011, 49, 5042—each incorporated herein by reference in its entirety). Generally, polyphosphonates are used as flame retardants (Lu, S. Y.; Hamerton, I. *Prog. Polym. Sci.* 2002, 27, 1661—incorporated herein by reference in its entirety), in the biomedical field as adhesion promoters to dental tissue (Moszner, N.; Salz, U.; Zimmermann, J. *Dent. Mater.* 2005, 21, 895; Xu, X.; Wang, R.; Ling. L.; Burgess, J. O. *J. Polym. Sci. Part A: Polym. Chem.* 2007, 45, 99—each incorporated herein by reference in its entirety) and bone (Erez, R.; Ebner, S.; Attali, B.; Shabat, D. *Bioorg. Med. Chem. Lett.* 2008, 18, 816; Alferiev, I.; Vyavahare, N.; Song, C.; Connolly, J.; Hinson, J. T.; Lu, Z.; Tallapragada, S.; Bianco, R.; Levy, R. *Biomaterials* 2001, 22, 2683; Wang, L.; Zhang, M.; Yang, Z.; Xu, B. *Chem. Commun.* 2006, 2795—each incorporated herein by reference in its entirety). pH-responsive bisphosphonates $R^1R^2C(PO_3H)_2$, analogs of pyrophosphates $O(PO_3H)_2$, are used as corrosion inhibitors (Gunasekaran, G.; Natarajan, R.; Muralidharan, V. S.; Rao, B. V. A. *Anti-Corros. Method. M.* 1997, 44, 248—incorporated herein by reference in its entirety) in concrete, coatings, rubber blends, etc, and complexing agents in oil industries (Graham, R.; Russell, G. *Bone* 2011, 49, 2—incorporated herein by reference in its entirety), as antiscalants to sequester calcium ions, and as inhibitors of bone resorption in bone-related diseases (Fleish, H.; Neuman, W. F. *Am. J. Physiol.* 1961, 1296—incorporated herein by reference in its entirety).

pH-responsive polyphosphonates bearing nitrogen such as protonated ($NH^+$) aminomethyl—and aminopropylphosphonate residues have been synthesized using a cyclopolymerization technique (Al-Hamouz, O. C. S.; Ali, S. A. *J. Polym. Sci., Part A: Polym. Chem.* 2012, 50, 3580; Ali S. A.; Al-Hamouz, O. C. S. *Polymer* 2012, 53, 3368; Ali, S. A.; Abu-Thabit, N.Y.; Al-Muallem, H. A. *J. Polym. Sc., Part A: Polym. Chem.* 2010, 48, 5693; Abu-Thabit, N. Y.; Kazi, I. W.; Al-Muallem, H. A.; Ali, S. A. *Eur. Polym. J.* 2011, 47, 1113— each incorporated herein by reference in its entirety). The cylopolymerization of a diallyl quaternary amine salt [$CH_2$=CH—$CH_2$)$_2$$NH^+$CH($PO_3$H)($PO_3^-$)] having bisphosphonate functionality with the P attached to the same carbon has been reported (see Riedelsberger above). Cyclopolymerization of a symmetric bisphosphonate diallyl quaternary ammonium salt having phosphorous atoms attached two different carbons has not yet been reported. Keeping in view the importance of phosphonates, herein the synthesis and cyclopolymerization of a new bisphosphonate monomer 4 bearing bis-3-phosphorylpropyl substituents is reported (see Scheme 1 herein). Ester hydrolysis of cyclopolymer 5 to pH-responsive 6 permits examination of solution properties, determination of acid dissociation constants and efficiency as an antiscalant to inhibit $CaSO_4$ scale formation in desalination plants.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the disclosure includes a symmetrically substituted cationic monomer.

Another embodiment includes a method for synthesizing and copolymerizing the cationic monomer to form a cationic polyelectrolyte (CPE) and a cationic polyacid (CPA).

Another embodiment includes a method in which dialysis of the cationic polyacid forms a pH-responsive polyzwitterionic acid (PZA).

Another embodiment includes a method in which the (PZA) undergoes pH-induced transformation and its converted into polyzwitterion/anion (±−) (PZAN), polyzwitterion/dianion (±=) (PZDAN), and polyzwitterion/trianion (±≡) (PZTAN).

Another embodiment includes using the PZA as an antiscalant in a Reverse Osmosis desalinization plant to inhibit or treat the formation of a scale.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 1A-1C show $^1$H NMR spectra of polymers in (+NaCl) in $D_2O$;

DETAILED DESCRIPTION OF THE EMBODIMENTS

Figures 2A, 2B, 2C:
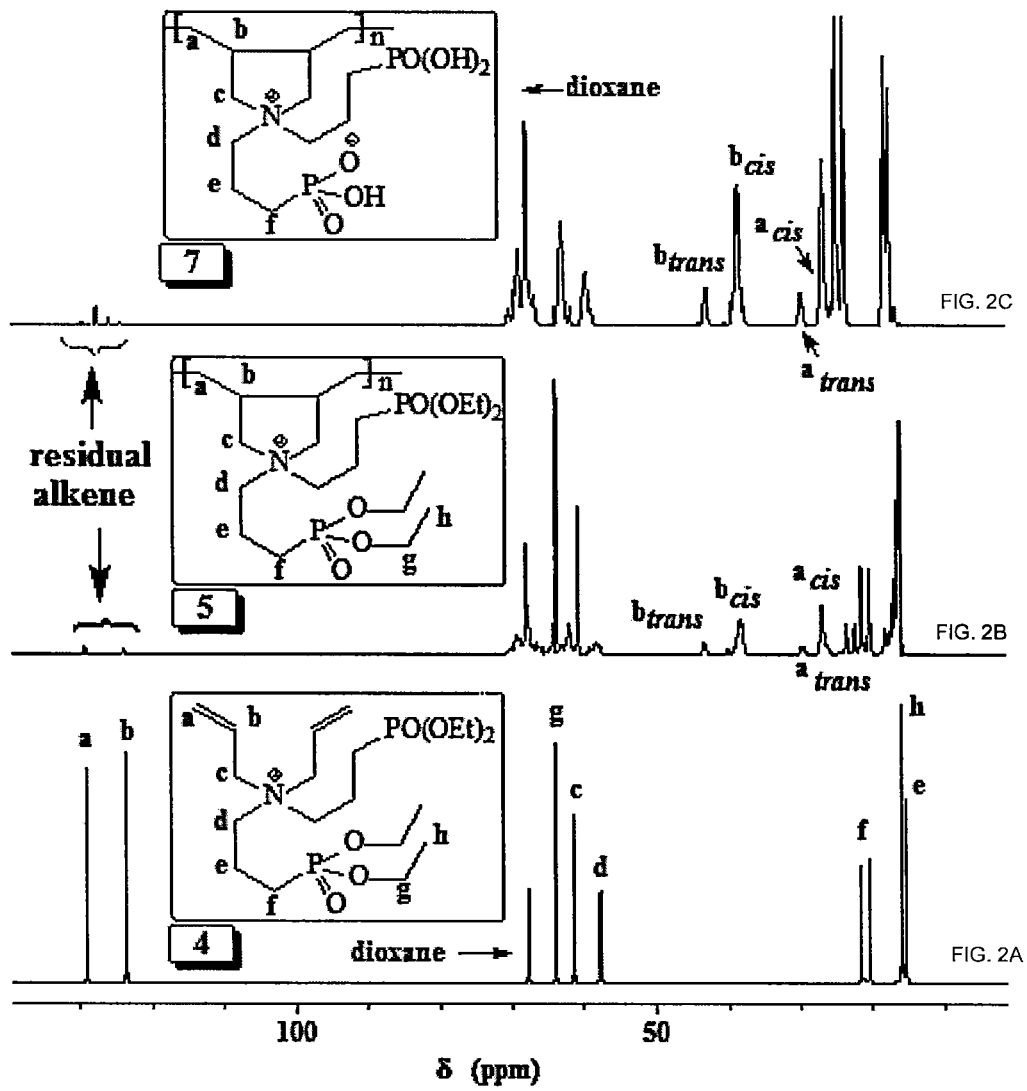
FIGS. 2A-2C show $^{13}$NMR spectra of polymers in (+NaCl) in $D_2O$.

Referring now to the drawings, wherein like reference numerals designate identical or corresponding parts throughout the several views.

The invention includes the cationic polyelectrolyte 4 having the following structure (I):

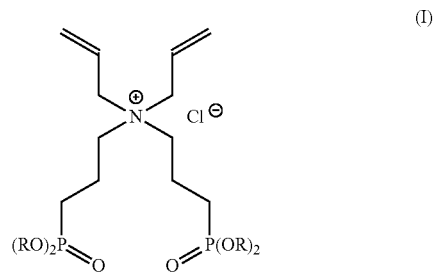

Zwitterionic monomer 4 of formula (I) is a cationic nitrogen-containing compound in which the nitrogen atom is bonded to two allyl units. The nitrogen atom is further bonded to two identical phosphopropyl groups through linking propyl groups with the formula for each terminal phosphonate group being (—P(O)(OH)$_2$ or —P(O)(O$R_2$) where the "R" group may be the same or different and is preferably a $C_1$-$C_6$ alkyl or $C_6$-$C_{12}$ aryl group selected from the group consisting of methyl, ethyl, propyl, butyl, pentyl, or hexyl or the aryl groups selected from the group consisting of phenyl, tolyl, xylyl, mesityl, naphthyl, biphenyl and any isomers thereof. "R" may be substituted or unsubstituted. Preferably the "R" group of the phosphonate group is an ethyl group.

$Cl^-$ is an anion and can be further represented as $Br^-$, $I^-$, $F^-$ or any other negatively charged derivative.

Scheme 1. Cyclopolymerization of diallylbisphosphonate monomer

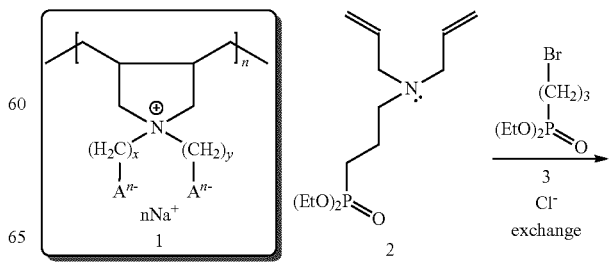

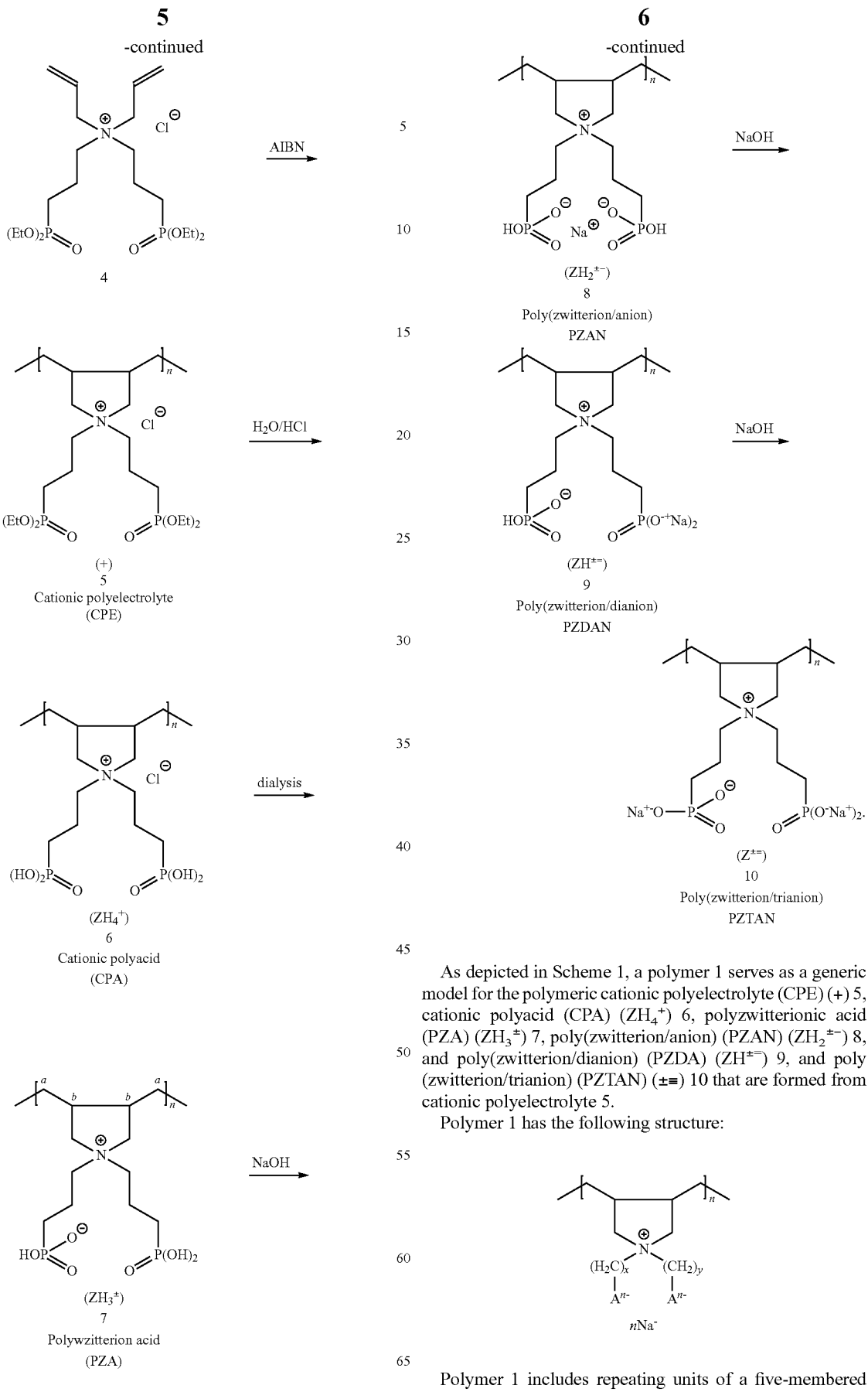

As depicted in Scheme 1, a polymer 1 serves as a generic model for the polymeric cationic polyelectrolyte (CPE) (+) 5, cationic polyacid (CPA) ($ZH_4^+$) 6, polyzwitterionic acid (PZA) ($ZH_3^\pm$) 7, poly(zwitterion/anion) (PZAN) ($ZH_2^{\pm-}$) 8, and poly(zwitterion/dianion) (PZDA) ($ZH^{\pm=}$) 9, and poly(zwitterion/trianion) (PZTAN) ($\pm\equiv$) 10 that are formed from cationic polyelectrolyte 5.

Polymer 1 has the following structure:

Polymer 1 includes repeating units of a five-membered heterocyclic ring having a nitrogen atom bonded to two linking units comprising identical phosphonate groups with the formula for each phosphonate group being (—P(O)(OH)$_2$ or —P(O)(OR)$_2$) where the "R" group is preferably an alkyl or aryl group selected from the group consisting of methyl, ethyl, propyl, butyl, pentyl, or hexyl or the aryl groups selected from the group consisting of phenyl, tolyl, xylyl, mesityl, naphthyl, biphenyl and any isomers thereof. "R" may be substituted or unsubstituted. Preferably the "R" group of the phosphonate group is an ethyl group. The phosphonate group and linking groups can be further represented in polymer 1 as —(CH$_2$)$_x$-A''$^-$. More specifically, the variable "x" represents the number of methylene units, and "x" is 3. The group "A''$^-$" represents a phosphonate group. Variable "n$^-$" represents the charge value of the corresponding phosphonate group and also the coefficient representing the number of atoms of the cationic counter ion. The "n" represents the number of repeating units of the corresponding polymer and "n" is at least 10, preferably at least 15, 20, 40, 80, or 100. More preferably, "n" is in the range of 20-1,500; 40-1,400; 80-1,300; or 100-1,200. Polymer 1 is preferably a homopolymer containing no comonomers or containing only one type of repeating unit and one or more different terminal groups. Cationic materials such as K$^+$, Cu$^+$, or Li$^+$ and dicationic materials such as Ca$^{2+}$, Cr$^{2+}$, Cu$^{2+}$, Fe$^{2+}$, Pb$^{2+}$, Mg$^{2+}$, Mn$^{2+}$, Hg$^{2+}$, Sr$^{2+}$, Sn$^{2+}$, or Zn$^{2+}$ may be used in place of Na$^+$.

As further depicted in Scheme 1, a solution of the monomer 2, which is a tertiary amine, diethyl 3-(diallylamino)propylphosphonate, is treated with diethyl 3-bromopropylphosphonate 3 to yield a monomeric zwitterion 4. The treatment of monomer 2 with 3 yields the resultant cationic phosphonate material. The monomeric cation 4 is the monomer bis[3-(diethoxyphosphoryl)propyl]diallylammonium chloride. The monomer is a cationic nitrogen-containing compound bonding to units where the phosphoryl group is of the formula C—P(O)(OR)$_2$ where the "R" group is preferably an alkyl group selected from the group consisting of methyl, ethyl, propyl, butyl, pentyl, or hexyl or an aryl group is selected from the group consisting of phenyl, tolyl, xylyl, mesityl, naphthyl, biphenyl and any isomers thereof. Preferably the "R" group of the phosphonate group is an ethyl group.

The monomeric cation 4 is then treated with a polymerizing agent. The polymerizing agent is preferably azobisisobutyronitrile (AIBN), which acts to initiate cyclopolymerization of the cationic monomer 4 to yield a cationic polyelectrolyte 5. The polyelectrolyte 5 contains the core structure following the model of polymer 1, further including the phosphoryl group.

The polyelectrolyte 5 is then treated with a solution of water and a concentrated inorganic acid, preferably HCl, to yield a cationic polyacid (PZA) (ZH$_4^+$) 6, which contains two hydroxy groups in the formula of the phosphonate group. (PZA) (ZH$_4^+$) 6 contains the structure following the model of polymer 1, further including the phosphonate group in the form of C—P(O)(OH)$_2$. Cationic polyacid 6 may be used as an antiscalant for example in reverse osmosis plants against mineral scales such as CaCO$_3$, CaSO$_4$, and Mg(OH)$_2$.

Treatment of (PZA) (ZH$_4^+$) 6 with dialysis deprotonates one of the hydroxy groups of the first phosphonate group to provide a polymeric material having an anionic charge. The anionically charged derivative of the of (PZA) (ZH$_4^+$) 6 is shown as polyzwitterion acid (PZA) (ZH$_3^\pm$) 7.

Treatment of (PZA) (ZH$_3^\pm$) 7 with an alkaline material, e.g. NaOH, KOH, Ca(OH)$_2$ and the like, more preferably with NaOH, deprotonates one of the hydroxy groups of the second phosphonate group to provide a polymeric material having a dianionic charge balanced by a counter ionic charge. The derivative of (PZA) (ZH$_3^\pm$) 7 is a poly(zwitterion/anion) (PZAN) (ZH$_2^{\pm-}$) 8.

Upon further treatment of (PZAN) (ZH$_2^{\pm-}$) 8 with additional base, the anionic oxygen atom of one of the phosphonate groups forms a (Na$^{+-}$O) complex bonded to the corresponding phosphorus atom to yield a dianionic charge. The dianionically charged derivative of the (PZAN) (ZH$_2^{\pm-}$) 8 is shown as poly(zwitterion/dianon) (PZDA) (ZH$^{\pm=}$) 9.

Upon further treatment of (PZDA) (ZH$^{\pm=}$) 9 with additional base the anionic oxygen atom of one of the second phosphonate group forms a second (Na$^{+-}$O) complex bonded to the corresponding phosphorus atom to yield a trianionic charge. The trianionically charged derivative of the (PZDA) (ZH$^{\pm=}$) 9 is shown as poly(zwitterion/trianon) PZTAN) (±≡) 10.

(PZA) (ZH$_4^+$) 6, (PZA) (ZH$_3^\pm$) 7, (PZAN) (ZH$_2^{\pm-}$) 8, and (PZDA) (ZH$^{\pm=}$) 9 may be used as antiscalants in reverse osmosis plants against mineral scales such as CaCO$_3$, CaSO$_4$, and Mg(OH)$_2$.

EXAMPLES

A Perkin Elmer Elemental Analyzer Series II Model 2400 and a Perkin Elmer 16F PC FTIR spectrometer were used to carry out Elemental analyses and record IR spectra, respectively. The $^{13}$C, $^1$H and $^{31}$P NMR spectra have been measured in D$_2$O (using HOD signal at δ 4.65 and dioxane $^{13}$C peak at δ 67.4 as internal standards) on a JEOL LA 500 MHz spectrometer. $^{31}$P was referenced with 85% H$_3$PO$_4$ in DMSO. Viscosity measurements have been made by Ubbelohde viscometer using CO$_2$-free water under N$_2$. A Sartorius pH Meter PB 11 For the potentiometric titrations was used to measure the pH of the solutions.

Tertiary butyl hydroperoxide (TBHP) (70 w/w % in water) from Fluka AG (Buchs, Switzerland) were used as received. A Spectra/Por membrane with a MWCO value of 6000-8000 Spectrum Laboratories, Inc was used for the dialysis. Diethyl 3-(diallylamino)propylphosphonate 2 was prepared as described by reacting diallylamine and 1-Bromo-3-(diethylphosphonato)propane (Ali, S. A.; Abu-Thabit, N. Y.; Al-Muallem, H. A. *J. Polym. Sc., A: Polym. Chem.*, 2010, 48, 5693—incorporated herein by reference in its entirety).

Synthesis of Monomer N-allyl-N,N-bis[3-(diethoxyphosphoryl)propyl]prop-2-en-1-aminium chloride (4) preferably occurs by the following method: A mixture of diethyl 3-(diallylamino)propylphosphonate 2 (20.2 g, 73.4 mmol) and diethyl 3-bromopropylphosphonate (3) (31.0 g, 119.7 mmol), K$_2$CO$_3$ (10.57 g, 76.6 mmol) in acetonitrile (120 cm$^3$) was stirred under N$_2$ at an oil-bath temperature of 95° C. for 96 h. After concentration, the residual liquid was taken up in water (40 mL) and washed with ether (3×50 mL). The aqueous layer was saturated with NaCl, then mixed with concentrated HCl (15 mL) and stirred using a magnetic stir-bar at room temperature for 10 min. The aqueous layer was extracted with CHCl$_3$ (3×50 mL). After removal of the solvent, the CHCl$_3$ extract was taken up in saturated NaCl solution (30 mL) and stirred for 30 min. The aqueous layer was then washed with a 2:1 ether/CH$_2$Cl$_2$ mixture (3×50 mL). Finally, the aqueous layer was extracted with CH$_2$Cl$_2$ (3×100 mL). The CH$_2$Cl$_2$-extract was dried (Na$_2$SO$_4$), concentrated and the residual pale yellow liquid was dried under vacuum to a constant weight (25.4 g, 71%). The monomer was found to be pure as indicated by the NMR spectrum. (Found: C, 48.6; H, 8.8; N, 2.7%. C$_{20}$H$_{42}$ClNO$_6$P$_2$ requires C, 49.03; H, 8.64; N, 2.86%); ν$_{max}$(KBr): 3422, 3081, 2984, 2909, 1644, 1471, 1444, 1242, 1163, 1026, 964, 875, 792, 752 and 661 cm$^{-1}$; δ$_H$ (D$_2$O) 1.21 (12H, t, J=7 Hz), 1.80-2.00 (8H, m), 3.20 (4H, m), 3.83 (4H, d, J=7.0 Hz), 4.03 (8H, m), 5.61 (4H, m), 5.88 (2H, m), (HOD: 4.65); δ$_C$ (D$_2$O) 15.52 (s, PCH$_2$CH$_2$), 16.10 (d, 2C, Me, $^3$J (PC) 6.2 Hz), 21.10 (d, PCH$_2$, $^1$J (PC) 142 Hz), 57.92 (d, PCH2CH2CH$_2$, $^3$J (PC) 16.5 Hz), 61.44 (2C, =CH—CH$_2$, s), 63.99 (d, 2C, OCH$_2$CH$_3$, $^2$J (PC) 6.2 Hz), 124.10 (2C, s, CH$_2$=CH), 129.42 (2C, s, CH$_2$=CH) (dioxane:

67.40 ppm); $\delta_P$ (202 MHz, D$_2$O): 30.94 (s). $^{13}$C spectral assignments were supported by DEPT 135 NMR analysis (FIGS. 1 and 2).

Acid hydrolysis of monomer 4 to cationic acid (CA) 11 preferably occurs by the following method: A solution of 4 (15 g, 30.6 mmol) in water (25 mL) and concentrated HCl (22 mL) was heated in a flask at 95° C. for 48 h. Removal of the solvent followed by dissolution of the residual liquid in methanol, and pouring into acetone gave cationic acid (CA) 11 as a thick liquid (dried under reduced pressure at 50° C.) (11.0 g, 95%). An analytical sample was made by keeping a portion of the thick liquid dissolved in a mixture of methnol/acetone in a freezer for two weeks to obtain 11 as highly hygroscopic white solid. Mp. 75-80° C. (Found: C, 37.8; H, 7.2; N, 3.6%. C$_{12}$H$_{26}$ClNO$_6$P$_2$ requires C, 38.16; H, 6.94; N, 3.71%); $\nu_{max}$ (neat) 3500-2500 (very broad), 2959, 1702, 1642, 1475, 1418, 1368, 1230, 1169, 995, 874, and 714 cm$^{-1}$. $\delta_H$ (D$_2$O) 1.51 (4H, dt, J=18.3 and 7.4 Hz), 1.75 (4H, m), 3.04 (4H, m), 3.64 (4H, d, J=7.3 Hz), 5.42 (4H, m), 5.72 (2H, m), (HOD: 4.65); $\delta_C$ (D$_2$O) 15.87 (2C, s, PCH$_2$CH$_2$), 23.32 2C, (d, PCH$_2$, $^1$J (PC) 140 Hz), 58.28 (2C, d, PCH$_2$CH$_2$CH$_2$, $^3$J (PC) 18.6 Hz), 61.37 (2C, =CH—CH$_2$, s), 124.10 (2C, s, CH$_2$=CH), 129.20 (2C, s, CH$_2$=CH) (dioxane: 67.40 ppm); $\delta_P$ (202 MHz, D$_2$O): 26.00 (m). $^{13}$C spectral assignments were supported by DEPT 135 NMR analysis.

The cyclopolymerization of monomer 4 or monomer 11 preferably occurs by the following method: The conditions for the polymerizations on a scale of 7.5 mmol of monomer were presented in Table I. Table I is presented below.

Cationic monomer 4, synthesized by reacting tertiary amine 2 with diethyl 3-bromopropylphosphonate (3), underwent cyclopolymerization to afford cationic polyelectrolyte (CPE) 5 in reasonable yields bearing in mind the difficulty in putting four rather bulky substituents on a five-membered ring (Scheme 1, Table I). Note that the isolated yields are lower than the $^1$H NMR yields as determined by the NMR analysis of the crude reaction mixture. This is attributed to the lower molar mass of the polymers as demonstrated by their low intrinsic viscosities, and as such a considerable portion of the polymer chains of lower masses escapes the dialysis bag having a molecular weight cut off of 6000-8000 g/mol. The involvement of the ethoxy group attached to the P atom in the chain transfer between polymer radical and monomer is one of the causes that leads to the lower yields and intrinsic viscosity values (Table I).[47]

As evident from Table I, initiator or monomer concentration does not seem to have any considerable effect on the polymer yields. Note that the hydrolyzed monomer (+) 11 (Entry 6, Table I, Scheme 2) on polymerization afforded zwitterionic (±) PZA 7 via CPA (+) 6 which is identical to that obtained from hydrolysis of CPE (+) 5 (Scheme 1).

TABLE I

Cyclopolymerization$^a$ of Monomers 4 and 11.

| Entry No. | Monomer (mmol) | Water (% w/w) | Initiator$^a$ (mg) | Temp (° C.) | Time (h) | Yield (%) NMR | Yield (%) isolated | [η]$^b$ (dL g$^{-1}$) |
|---|---|---|---|---|---|---|---|---|
| 1 | 4 (7.5) | 30 | APS (100) | 90 | 48 | 65 | 37 | 0.0545 |
| 2 | 4 (7.5) | 30 | APS (140) | 90 | 4 | 70 | 51 | 0.0475 |
| 3 | 4 (7.5) | 25 | APS (380) | 95 | 3 | 72 | 45 | 0.0417 |
| 4 | 4 (7.5) | 20 | TBHP (200) | 105 | 48 | 75 | 44 | 0.0496 |
| 5 | 4 (15) | 30 | APS (200) | 90 | 4 | 76 | 63 | 0.0484 |
| 6 | 11 (7.5) | 30 | APS (300) | 95 | 5 | 77 | 61 | — |

$^a$Polymerization reactions were carried out in aqueous solution of monomer 4 or 11 in the presence of ammonium persulfate (APS) or tert-butyl hydroperoxide (TBHP) at specified temperatures,
$^b$Viscosity of 1-0.25% polymer solution in 0.1M NaCl at 30.0 ± 0.1° C. was measured with Ubbelohde Viscometer (K = 0.005718).

The experiment under entry 5 was carried out on a larger scale of 15 mmol. Thus a solution of monomer 4 (7.35 g, 15 mmol) and water (3.15 g) in a 25-cm$^3$ round-bottom flask was purged with N$_2$, and after adding the initiator APS (200 mg), the mixture was stirred in the closed flask at 90° C. for 4 h. The reaction mixture dialyzed against deionized water for 24 h. The polymer solution was then freeze-dried to obtain CPE 5 as a light brown extremely hygroscopic polymer. The thermal decomposition: the color changed to dark brown and black at respective temperatures of 260° C. at 320° C. (Found: C, 48.7; H, 8.8; N, 2.8%. C$_{20}$H$_{42}$ClNO$_6$P$_2$ requires C, 49.03; H, 8.64; N, 2.86%); $\nu_{max}$ (KBr) 3420 (br), 2984, 2933, 2905, 1650, 1460, 1394, 1369, 1221, 1160, 1123, 1050, 1017, 968, 786, 698, 620 and 544 cm$^{-1}$. $\delta_P$ (202 MHz, D$_2$O): 32.89 (4%), 30.96 (72%), and 22.96 (24%). $^1$H NMR and $^{13}$C NMR spectra are shown in respective FIGS. 1 and 2.

Scheme 2. The monomer in different forms and protonation constants

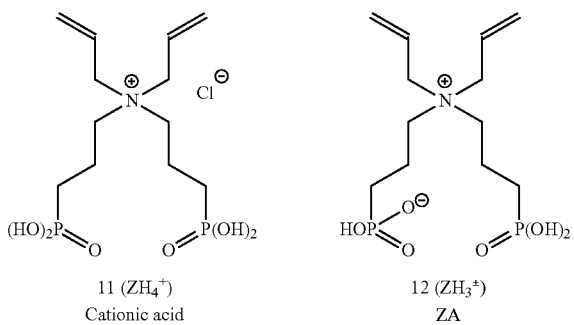

11 (ZH$_4^+$)
Cationic acid 12 (ZH$_3^\pm$)
ZA

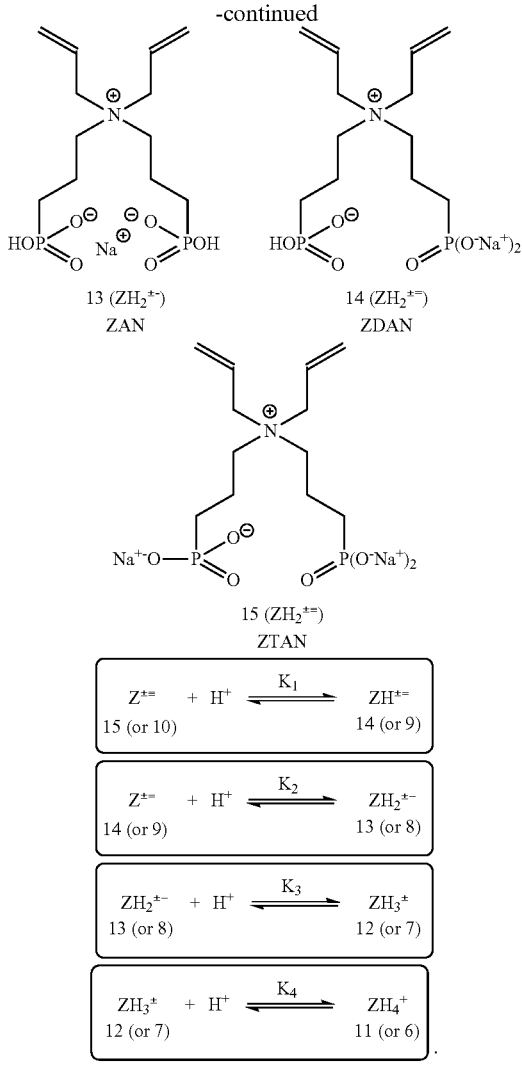

13 (ZH$_2^{+-}$)
ZAN 14 (ZH$_2^{+=}$)
ZDAN 15 (ZH$_2^{+≡}$)
ZTAN $$Z^{±≡} + H^+ \xrightleftharpoons{K_1} ZH^{±=}$$
15 (or 10)          14 (or 9)

$$Z^{±≡} + H^+ \xrightleftharpoons{K_2} ZH_2^{±-}$$
14 (or 9)          13 (or 8)

$$ZH_2^{±-} + H^+ \xrightleftharpoons{K_3} ZH_3^{±}$$
13 (or 8)          12 (or 7)

$$ZH_3^{±} + H^+ \xrightleftharpoons{K_4} ZH_4^{+}$$
12 (or 7)          11 (or 6)

log K$_i$ = pH - log [(1 - α)/α]     Eq 1
pH = log K$_i^o$ + n$_i$log [(1 - α)/α]     Eq 2
log K$_i$ = log K$_i^o$ + (n$_i$ - 1) log [(1 - α)/α]     Eq 3

Scheme 2 depicts the monomers of the corresponding polymers. The cationic acid 11 is the corresponding monomer to cationic polyacid 6; the zwitterionic acid 12 is the corresponding monomer to the polyzwitterionic acid 7; the zwitterion/anion 13 is the corresponding monomer to poly(zwitterion/anion) 8; the zwitterion/dianion 14 is the corresponding monomer to poly(zwitterion/dianion) 9; and the zwitterion/trianion 15 is the corresponding monomer to poly(zwitterion/trianion) 10.

The CPE (+) 5 was hydrolyzed in 6.7 M HCl to give water-soluble cationic polyacid (CPA) (+) 6, which on extended dialysis against deionized water gave water-insoluble PZA (±) 7. Neutralization of 7 with NaOH is expected to generate polyzwitterion-anion (PZAN) (±-) 8, polyzwitterion-dianion (PZDAN) (±=) 9 and polyzwitterion-trianion (PZTAN) (±≡) 10. Likewise, cationic monomer 4 was hydrolyzed to cationic acid (CA) 11 which upon neutralization with 1, 2 and 3 equivalents of NaOH would lead to zwitterions acid (ZA) (±) 12, zwitterion-anion (ZAN) (±-) 13, zwitterion-dianion (ZDAN) (±=) 14 and zwitterion-trianion (ZTAN) (±≡) 15.

Acid hydrolysis of CPE 5 to poly(zwitterion acid) (PZA) 7 preferably occurs by the following method: A solution of CPE 5 (3.5 g, 7.14 mmol) (derived from entry 5, Table I) in water (20 mL) and concentrated HCl (25 mL) was heated in a flask at 95° C. for 24 h or until the ester hydrolysis was complete as indicated by the absence of ethyl protons in the $^1$H NMR spectrum. The homogeneous mixture dialyzed against deionized water (to remove HCl) for 24 h. During dialysis, the polymer started to precipitates out as an oily material within 1 h. The resulting mixture was freeze-dried to obtain PZA 7 as a creamy white solid (2.3 g, 94%). The thermal decomposition: the color changed to brown and black at respective temperatures of 260° C. and 310-320° C. (Found: C, 41.9; H, 7.5; N, 3.9%. $C_{12}H_{25}NO_6P_2$ requires C, 42.23; H, 7.38; N, 4.10%); ν$_{max}$ (KBr) 3425 (br), 2952, 1651, 1463, 1416, 1234, 1146, 1058, 936, 756, 710 and 531 cm$^{-1}$. δ$_P$ (202 MHz, $D_2O$): 23.78. $^1$H NMR and $^{13}$C NMR spectra are shown in respective FIGS. 1A-1C and 2A-2C. FIGS. 1A-1C are $^1$H NMR spectrum of (a) 4, (b) 5, and (c) 7 (+NaCl) in $D_2O$. FIGS. 2A-2C are $^{13}$ NMR spectrum of (a) 4, (b) 5, and (c) 7 (+NaCl) in $D_2O$.

After stirring a mixture of PZ 5 or PZA 7 (2 w/w %) in a solvent at 70° C. (1 h), the solubility behavior was checked at 23° C. The results are given in Table II. Table II is presented below.

TABLE 2

Solubility[a,b] of CPE (+) 5 and PZA (±) 7

| Solvent | ε | 5 | 7 |
|---|---|---|---|
| Formamide | 111 | + | ± |
| Water | 78.4 | + | − |
| Formic acid | 58.5 | + | + |
| DMSO | 47.0 | + | − |
| Ethylene glycol | 37.3 | + | − |
| DMF | 37.0 | + | − |
| Methanol | 32.3 | + | − |
| Triethylene glycol | 23.7 | + | − |
| Acetic acid | 6.15 | + | − |

[a]2% (w/w) of polymer-water mixture (solution) was made after heating the mixture at 70° C. for 1 h and then cooling to 23° C.,
[b]'+' indicates soluble, '−' indicates insoluble, and '±' indicates partially soluble.

To a stirred mixture of PZA 7 (10 mg, 1 wt %) in deionized water (1 mL) was added NaCl in portions until it became soluble. The final solution was 0.71 M in NaCl. However addition of deionized water into the solution did not lead to a cloudy mixture; the polymer remained soluble.

Both CPE 5 and PZA 7 were observed to be stable up to around 260° C. While CPE (+) 5 was soluble in all the tested solvents; PZA (±) 7 was only partially soluble in formamide and soluble in formic acid but notably insoluble in water (Table II). This is expected since ((±) polyzwitterions are usually insoluble in salt-free water due to the strong electrostatic attractive interactions between the charges of opposite algebraic signs as well as dipolar interactions promoting intragroup, intra- and interchain associations. Water-insoluble PZs have been shown to be water-soluble with the assistance of NaCl which screens the zwitterionic charges from manifesting zwitterionic interactions thus permitting expansion of the polymer backbone and globule-to-coil transition ((Salamone, J. C.; Volksen, W.; Olson, A. P.; Israel, S. C. *Polymer* 1978, 19, 1157; Skouri, M.; Munch, J. P.; Candau, S. J.; Nyret, S.; Candau, F. *Macromolecules*, 1994, 27, 69—each incorporated herein by reference in its entirety). It was revealed that a 1 wt % PZA (±) 7 was soluble in the presence of NaCl with a minimum critical salt concentration (CSC) of 0.71 M. The polymer remained soluble afterwards; the addition of deionized water into the solution did not lead to a cloudy mixture. This could be attributed to the involvement of the equilibrium: [7 (ZH$_3^±$)⇌8 (ZH$_2^{±-}$)+H$^+$]; PZA (±)

7 with a $pK_a$ (i.e log $K_3$) value of ≈3.5 (vide infra) is expected to dissociate to PZAN (±−) 8 in which the anionic portion encourages water-solubility. Addition of water would lead to a decrease in the polymer concentration and thus promotes greater dissociation in the diluted solution. Solubility of PZA (±) 7 in formic acid could also be attributed to its protonation to water-soluble counterpart CPA (+) 6. This was supported by the observation during the dialysis: In the beginning, the polymer in 6.7 M HCl remained soluble owing to the presence of protonated form CPA (+) 6 while after 1 h of dialysis PZA (±) 7 started to precipitate as a result of the depletion of HCl from the dialysis bag (Scheme 1)

Procedure for the determination of the protonation constants ($K_1$, $K_2$ and $K_3$) of the polyzwitterion/trianion (PZ-TAN) 10 ($Z^{\pm=}$) and $K_1$, $K_2$ and $K_4$ of its corresponding monomer ZTAN 15 ($Z^{\pm=}$) by potentiometric titrations, carried out in an atmosphere of $N_2$ in $CO_2$-free water, is described elsewhere (Al-Muallem, H. A.; Wazeer M. I. M.; Ali, S. A. *Polymer*, 2002, 43, 4285—incorporated herein by reference in its entirety). A certain mmol of PZA 7 ($ZH_3^\pm$) or 11 ($ZH_4^+$) in 200 cm$^3$ of 0.0175 M NaCl was used in each trial (Tables 3 and 4). As the polymer was insoluble in salt-free water, it (≈100 mg) was first dissolved in 1 M NaCl (3.5 mL) and then diluted to 200 mL to make the polymer solution in 0.0175 M NaCl. For the sake of comparison the NaCl strength of water-soluble monomer 11 was also kept at 0.0175 M.

The Log $K_1$, Log $K_2$ and Log $K_3$ of the respective protonation of $^{2-}O_3P$—$X^+$—$PO_3^{2-}$ [in (±=) PZTAN 10], $^2O_3P$—$X^+$—$PO_3H^-$ [in (±=) (PZDAN) 9] and $^-HO_3P$—$X^+$—$PO_3H^-$ [(in (±−) plyzwitterion/anion (PZAN) 8] were calculated at each pH value by the Henderson-Hasselbalch eq 2 (Scheme 2) where the degree of protonation (α) is the ratios $[ZH^{\pm=}]_{eq}/[Z]_o$, $[ZH_2^{\pm-}]_{eq}/[Z]_o$ and $[ZH_3^\pm]_{eq}/[Z]_o$, respectively. The $[ZH^{\pm=}]_{eq}$, $[ZH_2^{\pm-}]_{eq}$ and $[ZH_3^\pm]_{eq}$ represent the respective equilibrium concentrations of the first (9), second (8) and third protonated species (7) whereas $[Z]_o$ describes the initial concentration of repeating units.

For the determination of the third step [8 ($ZH_2^{\pm-}$)+$H^+$⇌7 ($ZH_3^\pm$)] protonation constant (log $K_3$) using the titration of PZA 7 [$ZH_3^\pm$] with NaOH, α represents the ratio $[ZH_3^\pm]_{eq}/[Z]_o$ whereby $[Z]_o$ and $[ZH_3^\pm]_{eq}$ are related by $[ZH_3^\pm]_{eq} = [Z]_o—C_{OH^-}—[H^+]+[OH^-]$, where $C_{OH^-}$ represent the added NaOH concentration. The equilibrium [$H^+$] and [$OH^-$] values were calculated from the pH value. Continuing the titration, the second step [9 ($ZH^{\pm=}$)+$H^+$⇌8 ($ZH_2^{\pm-}$)] protonation constant (log $K_2$) was determined using volume of the titrant after deducting the equivalent volume from the total volume. In this case, α represents the ratio $[ZH_2^{\pm-}]_{eq}/[Z]_o$ whereby $[ZH_2^{\pm-}]_{eq}$ equals $[Z]_o—C_{OH^-}—[H^+]+[OH^-]$. Finally the titration is ended by determination of the first step [10 ($Z^{\pm=}$)+$H^+$⇌9 ($ZH^{\pm=}$)] protonation constant (log $K_1$) using volume of the titrant after deducting the two-equivalent volume from the total volume. In this case, α represents the ratio $[ZH^{\pm=}]_{eq}/[Z]_o$ whereby $[ZH^{\pm=}]_{eq}$ equals $[Z]_o—C_{OH^-}—[H^+]+[OH^-]$. The fourth step [7 ($ZH_3^\pm$)+$H^+$⇌6 ($ZH_4^+$)] protonation constant (log $K_4$) using the titration of PZA 7 [$ZH_3^\pm$] with HCl was not carried out since PZA 7 [$ZH_3^\pm$] is simultaneously involved in two equilibia: [8 ($ZH_2^\pm$)+$H^+$⇌7 ($ZH_3^\pm$)] for log $K_3$ and [7 ($ZH_3^\pm$)+$H^+$⇌6 ($ZH_4^+$)] for log $K_4$. Simultaneous protonation and deprotonation of PZA 7 owing to the proximity of the log $K_3$ and log $K_4$ values made it difficult to determine the later.

The fact presented above regarding log $K_3$ and log $K_4$ values was corroborated during the titration of the $H_2O_3P$—$X^+$—$PO_3H_2$ in cationic monomer 11 ($ZH_4^+$) Cl$^-$ with NaOH. The concentration of $H^+$ ions present (as determined from pH) at the beginning far exceeded the initial concentration $[Z]_o$ of the monomer. This implied that both the $PO_3H_2$ in 11 ($H_2O_3P$—$X^+$—$PO_3H_2$) Cl$^-$ are simultaneously deprotonated to a large extent to make the combined $H^+$ concentration higher than that of $[Z]_o$. An approximate value of log $K_4$ for the fourth step protonation [12 ($ZH_3^\pm$)+$H^+$⇌11 ($ZH_4^+$)] was determined in a small window of α using 2$[Z]_o$ instead of $[Z]_o$ as the initial concentration of the monomer since both the $PO_3H_2$ in 11 ($H_2O_3P$—$X^+$—$PO_3H_2$) Cl$^-$ are involved in protonation and deprotonation. Log $K_3$ for the monomer could not be determined. Continued titration with NaOH led to the determination of Log $K_2$ and Log $K_1$ using volume of the titrant after deducting two-equivalent and three-equivalent volumes, respectively, from the total volume.

Eq 3 (Scheme 1) describes the apparent basicity constants of anionic centers where log $K_i^o$=pH at α=0.5 and $n_i$=1 in the case of sharp basicity constants. The '$n_1$' and log $K_i^o$ as the respective slope and intercept were determined from the linear regression fit of pH vs. log $[(1-\alpha)/\alpha]$. Protonation at the same time of the three basic sites: —$PO_3^=$ in $^{2-}O_3P$—$X^+$—$PO_3^{2-}$ (log $K_1$: 10.74), —$PO_3^=$ in $^{2-}O_3P$—$X^+$—$PO_3H^-$ (log $K_2$: 8.12) and $PO_3H^-$ in $^+HO_3P$—$X^+$—$PO_3H^-$ (log $K_3$: 3.51) (Table III) is not likely due to differences of their basicity constants by more than 2.5 orders of magnitude (vide infra). Note that basicity constant log K of any base B is the $pK_a$ of its conjugate acid $BH^+$. Table III is presented below.

TABLE III

Experimental Details for the Determination of Basicity Constants Using Polymer PZA 7 ($ZH_3^\pm$) in 0.0175M NaCl at 23° C.

| run | $ZH_3^\pm$ (mmol) | $C_T^a$ (mol dm$^{-3}$) | α-range | pH-range | Points[b] | Log $K_i^{oc}$ | $n_i^c$ | $R^{2,d}$ |
|---|---|---|---|---|---|---|---|---|
| Polymer 7 | | | | | | | | |
| 1 | 0.2959 (7: $ZH_3^\pm$) | −0.09690 | 0.88-0.34 | 9.15-11.25 | 16 | 10.78 | 1.88 | 0.9981 |
| 2 | 0.2652 ($ZH_3^\pm$) | −0.09690 | 0.84-0.39 | 9.36-11.12 | 18 | 10.69 | 1.90 | 0.9946 |
| 3 | 0.2324 ($ZH_3^\pm$) | −0.09690 | 0.79-0.39 | 9.66-11.14 | 18 | 10.75 | 1.98 | 0.9963 |
| Average | | | | | | 10.74 (5) | 1.92 (5) | |

Log $K_i^e$ = 10.74 + 0.92 log $[(1 - \alpha)/\alpha]$ For the reaction:
$$Z^{\pm=} + H^+ \underset{}{\overset{K_1}{\rightleftharpoons}} ZH^{\pm=}$$

TABLE III-continued

Experimental Details for the Determination of Basicity Constants Using Polymer
PZA 7 ($ZH_3^+$) in 0.0175M NaCl at 23° C.

| run | $ZH_3^\pm$ (mmol) | $C_T{}^a$ (mol dm$^{-3}$) | α-range | pH-range | Points[b] | Log $K_i{}^{oc}$ | $n_i{}^c$ | $R^2$,[d] |
|---|---|---|---|---|---|---|---|---|
| Polymer 7 | | | | | | | | |
| 1 | 0.2959 (7: $ZH_3^+$) | −0.09690 | 0.87-0.20 | 7.38-8.64 | 12 | 8.10 | 0.91 | 0.9975 |
| 2 | 0.2652 ($ZH_3^+$) | −0.09690 | 0.92-0.14 | 7.30-8.78 | 15 | 8.14 | 0.85 | 0.9941 |
| 3 | 0.2324 ($ZH_3^+$) | −0.09690 | 0.92-0.19 | 7.31-8.67 | 13 | 8.11 | 0.87 | 0.9877 |
| Average | | | | | | 8.12 (2) | 0.88 (3) | |

Log $K_2{}^e$ = 8.12 − 0.12 log [(1 − α)/α] For the reaction:

$$ZH^{\pm=} + H^+ \overset{K_2}{\rightleftharpoons} ZH_2^{\pm-}$$

| | | | | | | | | |
|---|---|---|---|---|---|---|---|---|
| Polymer 7 | | | | | | | | |
| 1 | 0.2959 (7: $ZH_3^+$) | −0.09690 | 0.58-0.31 | 3.21-4.65 | 17 | 3.56 | 3.06 | 0.9914 |
| 2 | 0.2652 ($ZH_3^+$) | −0.09690 | 0.56-0.32 | 3.23-4.55 | 16 | 3.51 | 3.07 | 0.9959 |
| 3 | 0.2324 ($ZH_3^+$) | −0.09690 | 0.55-0.31 | 3.28-4.55 | 14 | 3.45 | 3.05 | 0.9924 |
| Average | | | | | | 3.51 (6) | 3.06 (1) | |

Log $K_3{}^e$ = 3.51 + 2.06 log [(1 − α)/α] For the reaction:

$$ZH_2^{\pm-} + H^+ \overset{K_3}{\rightleftharpoons} ZH_3^{\pm}$$

[a] Titrant concentration (negative values indicate titrations with NaOH),
[b] Number of data points from titration curve,
[c] Values in the parentheses are standard deviations in the last digit,
[d] R = Correlation coefficient.
[e] log $K_i$ = log $K_i^o$ + ($n_i$ − 1) log [(1 − α)/α].

Antiscalant behavior of PZA 7 was evaluated in supersaturated $CaSO_4$ solution containing 2,600 and 6,300 ppm of $Ca^{2+}$ and $SO_4^{2-}$, respectively. This is 3 times the concentration in 1 CB (concentrated brine) of a reject brine at a Reverse Osmosis plant (Butt, F. H.; Rahman, F.; Baduruthamal, U. *Desalination* 1995, 103, 189—incorporated herein by reference in its entirety) Solutions containing $Ca^{2+}$ and $SO_4^{2-}$ ions equals to that in 6 CB were prepared by dissolving the calculated amount of $CaCl_2$ and $Na_2SO_4$, respectively, in deionized water. To a solution of 6 CB calcium chloride (60 mL) containing PZA 7 (20 ppm) in a round bottom flask at 40° C.±1° C. stirred at 300 rpm using a magnetic stir-bar, a preheated (40° C.) solution of 6 CB sodium sulfate (60 mL) was added quickly. Conductivity measurements of the resultant solution containing 10 ppm of PZA 6 were made at an interval of every 10 min initially to quantify the effectiveness of newly developed antiscalant PZA 6. The precipitation of $CaSO_4$ is indicated by a drop in conductivity. Visual inspection was carefully done to see any turbidity arising from precipitation.

Cationic monomer 4, synthesized by reacting tertiary amine 2 with diethyl 3-bromopropylphosphonate (3), underwent cyclopolymerization to afford cationic polyelectrolyte (CPE) 5 in reasonable yields bearing in mind the difficulty in putting four rather bulky substituents on a five-membered ring (Scheme 1, Table I). Note that the isolated yields are lower than the $^1$H NMR yields as determined by the NMR analysis of the crude reaction mixture. This is attributed to the lower molar mass of the polymers as demonstrated by their low intrinsic viscosities, and as such a considerable portion of the polymer chains of lower masses escapes the dialysis bag having a molecular weight cut off of 6000-8000 g/mol. The involvement of the ethoxy group attached to the P atom in the chain transfer between polymer radical and monomer is one of the causes that leads to the lower yields and intrinsic viscosity values (Table I) (Pike, R. M.; Cohen, R. A. *J. Polym. Sci.,* 1960, 44, 531—incorporated herein by reference in its entirety).

As evident from Table I, initiator or monomer concentration does not seem to have any considerable effect on the polymer yields. Note that the hydrolyzed monomer (+) 11 (Entry 6, Table I, Scheme 2) on polymerization afforded zwitterionic (±) PZA 7 via CPA (+) 6 which is identical to that obtained from hydrolysis of CPE (+) 5 (Scheme 1).

The CPE (+) 5 was hydrolyzed in 6.7 M HCl to give water-soluble cationic polyacid (CPA) (+) 6, which on extended dialysis against deionized water gave water-insoluble PZA (±) 7. Neutralization of 7 with NaOH is expected to generate polyzwitterion-anion (PZAN) (±−) 8, polyzwitterion-dianion (PZDAN) (+=) 9 and polyzwitterion-trianion (PZTAN) (=≡) 10. Likewise, cationic monomer 4 was hydrolyzed to cationic acid (CA) 11 which upon neutralization with 1, 2 and 3 equivalents of NaOH would lead to zwitterions acid (ZA) (±) 12, zwitterion-anion (ZAN) (±−) 13, zwitterion-dianion (ZDAN) (+=) 14 and zwitterion-trianion (ZTAN) (±≡) 15.

Both CPE 5 and PZA 7 were observed to be stable up to around 260° C. While CPE (+) 5 was soluble in all the tested solvents; PZA (±) 7 was only partially soluble in formamide and soluble in formic acid but notably insoluble in water (Table II). This is expected since ((±) polyzwitterions are usually insoluble in salt-free water due to the strong electrostatic attractive interactions between the charges of opposite algebraic signs as well as dipolar interactions promoting intragroup, intra- and interchain associations. Water-insoluble PZs have been shown to be water-soluble with the assistance of NaCl which screens the zwitterionic charges from manifesting zwitterionic interactions thus permitting expansion of the polymer backbone and globule-to-coil transition It was revealed that a 1 wt % PZA (±) 7 was soluble in the presence of NaCl with a minimum critical salt concentration (CSC) of 0.71 M. The polymer remained soluble afterwards; the addition of deionized water into the solution did not lead to a cloudy mixture. This could be attributed to the involvement of the equilibrium: [7 ($ZH_3^+$)⇌8 ($ZH_2^{\pm-}$)+$H^+$]; PZA (+) 7 with a p$K_a$ (i.e log $K_3$) value of ≈3.5 (vide infra) is expected to dissociate to PZAN (±−) 8 in which the anionic portion encourages water-solubility. Addition of water would lead to a decrease in the polymer concentration and thus promotes greater dissociation in the diluted solution. Solubility of PZA (±) 7 in formic acid could also be attributed to its protonation to water-soluble counterpart CPA (+) 6. This was supported by the observation during the dialysis: In the beginning, the polymer in 6.7 M HCl remained soluble owing to the presence of protonated form CPA (+) 6 while after 1 h of dialysis PZA (±) 7 started to precipitate as a result of the depletion of HCl from the dialysis bag (Scheme 1).

The strong IR absorptions of monomer 4 at 1163 cm$^{-1}$ and 1026 cm$^{-1}$ were attributed to the stretching frequency of P=O and P—O—C, respectively. For CPE 5 the corresponding absorption appeared at 1160 and 1050 cm$^{-1}$. The vibration frequencies at 1146 and 1169 cm$^{-1}$ were assigned to the respective stretching frequency of P=O of hydrolyzed polymer 7 and monomer 11. FIGS. 1 and 2 show the $^1$H and $^{13}$C NMR spectra of 4, 5, and 7, respectively. The DEPT 135 NMR analysis supported the assignments of the $^{13}$C signals. The absence of the OCH$_2$CH$_3$ signals in the spectra of 7 indicates its removal by hydrolysis (FIGS. 1$c$ and 2$c$). Polymers 5 or 7 even after extended dialysis contains ≈4% residual alkene presumably as a result of a certain portion of chain propagation without cyclization. The integration of the $^{13}$C (FIGS. 2$b$ and 2$c$) as well as $^{31}$P peaks of CPE 5 (see experimental) revealed a 75/25 cis-trans ratio of the configurational isomers of pyrrolidinium ring at $C_{b,b}$ which is similar to the earlier findings (Scheme 1) (Higgs, P. G.; Joanny J. F. *J. Chem. Phys.* 1991, 94, 1543—incorporated herein by reference in its entirety).

Eq. 4 was developed to give a mathematical expression to rationalize the solution behavior of symmetrically or asymmetrically charged ionic polymers (Everaers, R.; Johner, A.; Joanny, J-F. *Europhys. Lett.* 1997, 37, 275; Candau, F.; Joanny, J-F. In Polyampholytes (Properties in Aqueous Solution); Salamone J. C., Ed.; CRC Press: Boca Raton, Fla., 1996, vol. 7. p. 5462-76; Wittmer, J.; Johner, A.; Joanny, J-F. *Europhys. Lett.* 1993, 24, 263—each incorporated herein by reference in its entirety)

$$v^* = -\frac{\pi(fI_B)^2}{\kappa_S} + \frac{4\pi I_B \Delta f^2}{\kappa_S^2} \quad (4)$$

where f is the total fraction of charged monomers, Δf is the charge imbalance, $I_B$ is the Bjerrum length, and $\kappa_S$ is the Debye-Huckel screening parameter, and v* is the excluded volume—a negative or a positive value of which indicates chain contraction or expansion, respectively. For symmetrically charged polymers i.e. polymers having equal number of charges of both algebraic signs, the second term in eq. 4 is eliminated by virtue of Δf=0; hence a negative excluded volume (v*) indicates contraction to a collapsed coil. In the event of charge imbalance (i.e. Δf≠0), the second term in eq. 4, which describes the shielding of the Coulombic repulsive interactions, would play a role and in case of its domination over the first term may lead to expansion of the polymer chain to a semicoil owing to a positive v* value.

Figure 3:
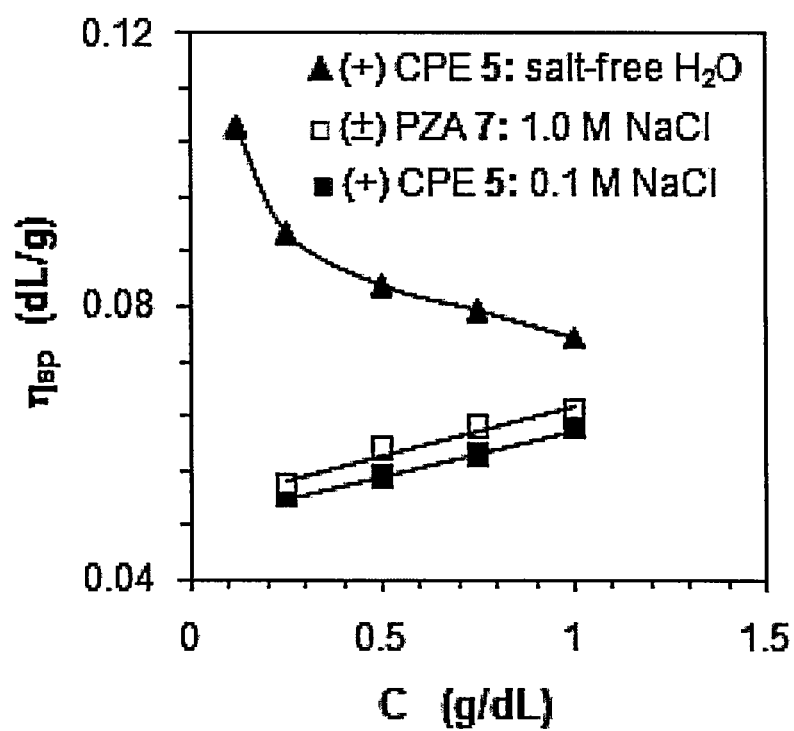
FIG. 3 shows a diagram demonstrating the viscosity behavior in 0.1 M NaCl of different polymers.

FIG. 3 is a graph using an Ubbelohde Viscometer at 30° C. that shows the viscosity behavior of (+) CPE 5 in ▲ salt-free water, □ (±) PZA7 in 1 M NaCl, ■ (+) CPE 5 in 0.1 M NaCl. (Polymer used and derived from entry 5, Table I). FIG. 3 shows the viscosity behavior of 5 and 7 in salt-free and salt-added water. The viscosity plot of CPE (+) 5 resembles that of a polyelectrolyte i.e. concave upwards in salt-free water and linear in 0.1 M NaCl. The viscosity plot of PZA (±) 7 in 1 M NaCl remain linear and it has higher viscosity values than the CPE (+) 5 in 0.1 M NaCl. Note that PZA (±) 7 is insoluble in salt-free water while soluble in the presence of NaCl with a CSC value of 0.71 M (vide supra).

Figure 4:
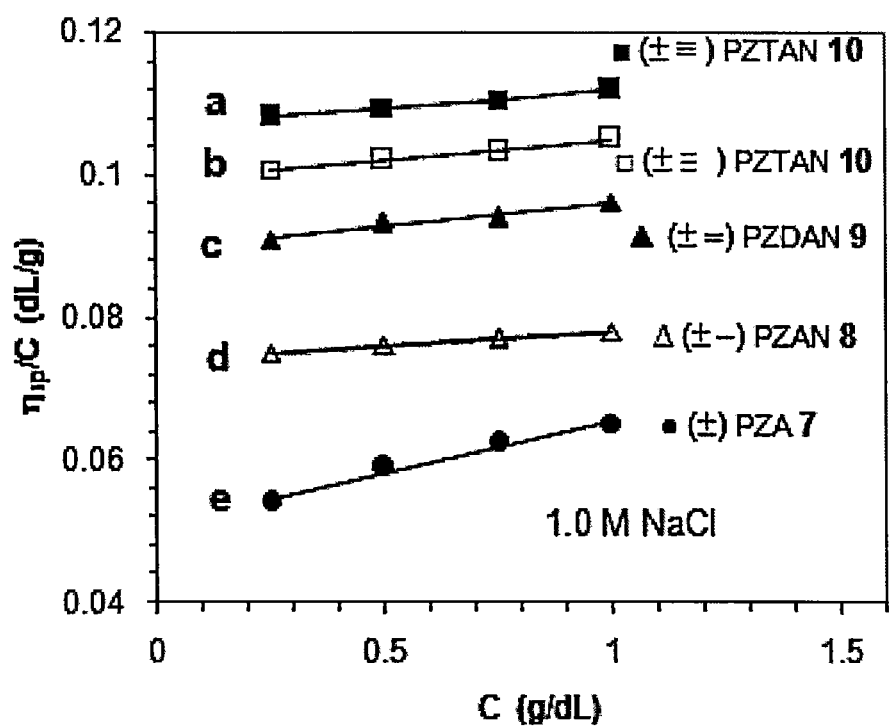
FIG. 4 shows a diagram demonstrating the viscosity behavior in 0.1 M NaCl of different polymers.

For the purpose of comparison, the viscosity of behaviors in 1 M NaCl of (±) PZA 7, (±−) PZAN 8, (±=) PZDAN 9, and (±≡) PZTAN 10 are shown in FIG. 4. FIG. 4 is a graph using an Ubbelohde Viscometer at 30° C. that shows the viscosity behavior in 1 M NaCl of: (a) ■ (±≡) PZTAN 10 (PZA 7+4 equivalents NaOH), (b) □ (±≡) PZTAN 10 (PZA 7+3 equivalents NaOH), (c) ▲ (±=) PZDAN 9, (d) Δ (±−) PZAN 8 and (e) ● (±) PZA 7. (All polymers are derived from entry 5, Table I). All the polymers have identical molar mass as a result of all being derived from the same polymer sample from entry 5, Table I. The viscosity values increase in the order: (±) 7<(±−) 8<(±=) 9<(±≡) 10. This is line with the increase in charge imbalance in going from 7 to 10 which in turn makes v* progressively less negative (or more positive) owing to contribution of the second term in eq. 4 resulting in expansion of the polymer chains hence increase in viscosities. (±≡) PZTAN 10 in the presence of 1 equivalent NaOH has higher viscosity values (FIG. 4$a$) than those in its absence (FIG. 4$b$). (±≡) 10 in aqueous solution is involved in the equilibrium: [10 (Z$^{±≡}$)+H$_2$O⇌9 (ZH$^{±=}$)+OH$^-$]; in the presence of OH$^-$ the equilibrium is shifted towards left thereby increasing the proportion of (±≡) 10, overall charge imbalance, v* value, and viscosity.

Figure 5:
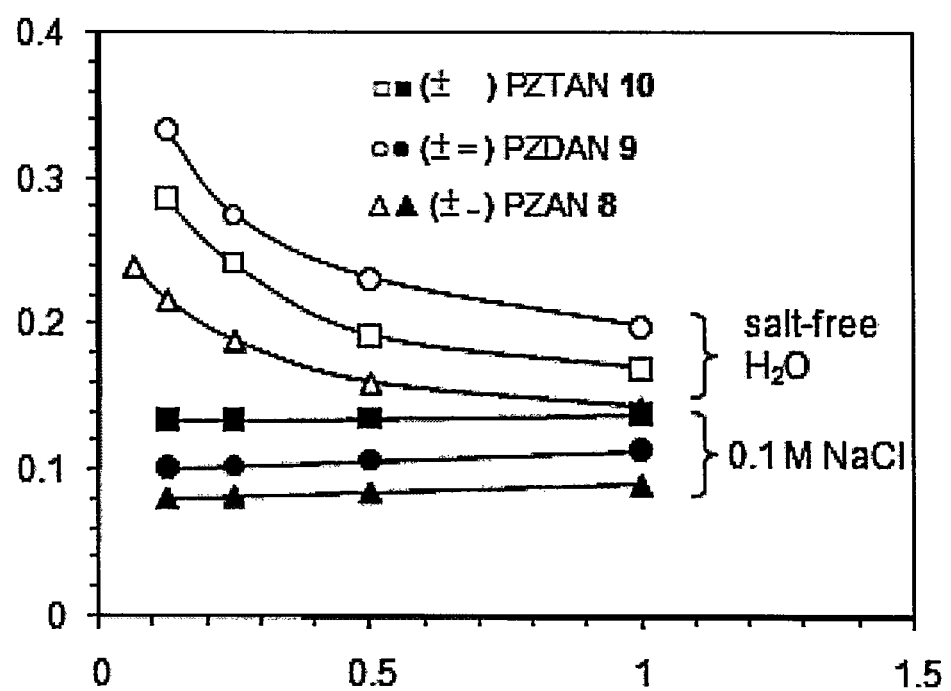
FIG. 5 shows a diagram demonstrating the viscosity behavior in salt-free water of different polymers.

FIG. 5 is a graph using an Ubbelohde Viscometer at 30° C. that shows the viscosity behavior in salt-free water and 0.1 M NaCl of: □■ (±≡) PZTAN 10, ○● (±=) PZDAN 9, and Δ▲ (±−) PZAN 8 (e) ● (±) PZA7. (All polymers are derived from entry 5, Table I). FIG. 5 displays the viscosity behaviors of (±−) PZAN 8, (±=) PZDAN 9, and (±≡) PZTAN 10 in salt-free water and 0.1 M NaCl. For a pure electroneutral zwitterions (±), the viscosity plots are linear either in salt-free or salt-added solutions. Unlike PZs (±), viscosity plots of 8, 9 and 10 are concave upwards like cationic or anionic polyelectrolytes in salt-free water. This indicates the controlling of viscosity behaviors by the anionic portions of the polymers. As expected with the increase in charge imbalance the viscosity values increase in the order: 8<9<10. In 0.1 M NaCl the viscosity plots became linear with the same order of increase in the [η]s. The [η] of 8, 9, and 10 were determined to be 0.074, 0.089 and 0.099 dL/g in 1 M NaCl (FIG. 4), respectively, while the corresponding values in 0.1 M NaCl were found to be 0.0780, 0.099 and 0.133 dL/g (FIG. 5). While the polymer chain is contracted owing by the shielding of the repulsive forces among the anionic charges by Na$^+$ ions (polyelectrolyte effect), the presence of salt leads to its expansion as a result of disruption of the attractive zwitterionic interactions by shielding of the (±) charges by Na$^+$ and Cl$^-$ ions (anti-polyelectrolyte effect). The polyelectrolyte effect is slightly more pronounced as indicated by the slightly higher values of [η]s in 0.1 M NaCl as compared to those in 1 M NaCl. Based on the pK$_a$ value of 3.51 in 0.0175 M NaCl (vide infra), the extent of dissociation of —PO$_3$H$_2$ of H$_2$O$_3$P—X$^+$—PO$_3$H$^-$ in (±) PZA 7 (Table III) to —PO$_3$H$^-$ of (±−) PZAN 8 in solutions having polymer concentration of 1, 0.75, 0.5, and 0.25 g/dL is calculated to be 9.8, 11, 14, and 19 mol %, respectively. The viscosity plot of (±) PZA 7 is thus expected to be concave upwards in salt added solutions as result of increasing charge imbalance with the decrease in polymer concentrations (FIG. 3). However the contraction and expansion caused by shielding of the respective excess anionic (−) and zwitterionic (±) charges leads to linearity of the plot. The problem of dissociation does not arise in the cases of (±−) PZAN 8 and (±=) PZDAN 9 since their respective p$K_a$ values of 8.12 and 10.74 (Table III) translate into negligible amount of dissociations to 9 and 10 and as such the viscosity plots in salt-added solutions remain linear.

Figure 6:
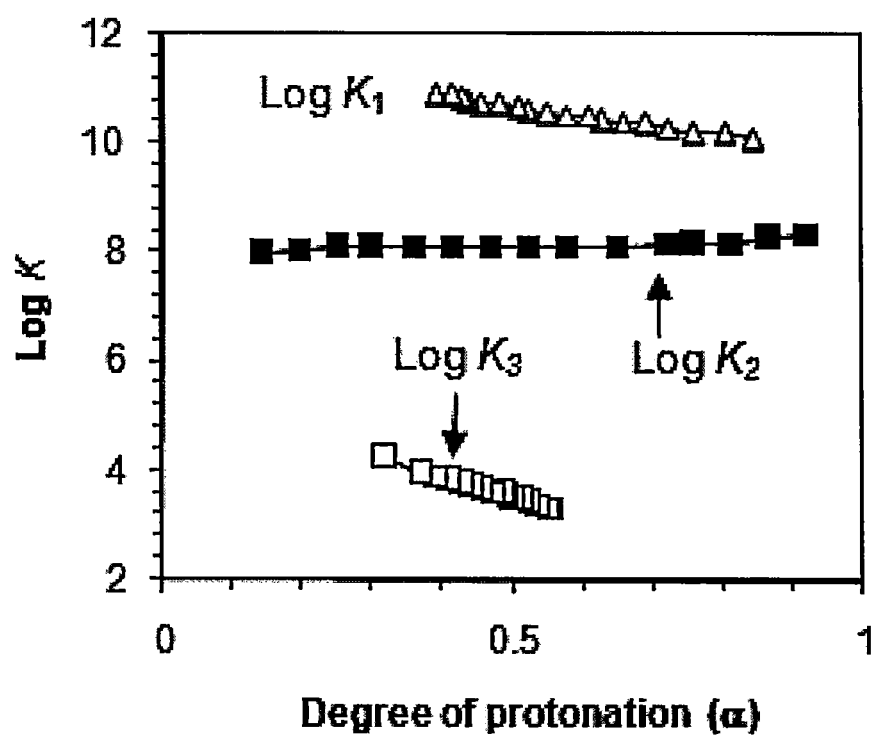
FIG. 6 shows a plot for the apparent log $K_1$, log $K_2$ and log $K_3$ versus degree of protonation (α) for (±≡) PZDAN 9.

The basicity constants log $K_1$ (10.74), log $K_2$ (8.12) and log $K_3$ (3.51) for the respective protonation of $^{2-}O_3P$—$X^+$—$PO_3^{2-}$ in (±=) PZTAN (10), $^{2-}O_3P$—$X^+$—$PO_3H^-$ in (±=) PZDAN 9 and $^-HO_3P$—$X^+$—$PO_3H^-$ in (±−) PZAN 8 were determined (Table III). The log $K_4$ for the protonation of $H_2O_3P$—$X^+$—$PO_3H^-$ in (±) PZA 7 could not be determined owing to its proximity to the value of log $K_3$ (see experimental). The log $K_1$, log $K_2$ and log $K_4$ for the monomer unit (±≡) 15 were determined to be 9.78, 7.43 and 2.30, respectively (Table IV). Table IV is presented below.

electrostatic field force that encourages protonation. Note that log $K_2$ associated with the transformation of $^{2-}O_3P$—$X^+$—$PO_3H^-$ [(±=) 9] to $^-HO_3P$—$X^+$—$PO_3H^-$ [(±−) 8] remained almost constant (n=0.88) with the change in α (FIG. 6).

Note that the highest polyelectrolyte index i.e. the highest n value of 3.06 belongs to $n_3$ associated with the transformation of polyzwitterion/anion (±−) 8 to electroneutral polyzwitterions (±) 7 (Table III). This could be attributed to the beneficial entropy effects (Barbucci, R.; Casolaro, M.; Ferruti, P.; Nocentini, M. *Macromolecules* 1986, 19, 1856—incorporated herein by reference in its entirety) associated with the release of a greater number of hydrated water molecules from the repeating unit during protonation. This is

TABLE IV

Experimental Details for the for the Determination of Basicity Constants Using Monomer ZDA (ZH$_4^+$) 11 in 0.0175M NaCl at 23° C.

| run | ZH$_4^+$ (mmol) | $C_T^a$ (mol dm$^{-3}$) | α-range | pH-range | Points$^b$ | Log $K_l^{oc}$ | $n_l^c$ | $R^{2,d}$ |
|---|---|---|---|---|---|---|---|---|
| Monomer 11 | | | | | | | | |
| 1 | 0.2912 (6: ZH$_4^+$) | −0.09690 | 0.91-0.17 | 8.70-10.65 | 18 | 9.84 | 1.07 | 0.9937 |
| 2 | 0.2507 (ZH$_4^+$) | −0.09690 | 0.84-0.12 | 9.00-10.6 | 16 | 9.76 | 1.04 | 0.9903 |
| 3 | 0.2102 (ZH$_4^+$) | −0.09690 | 0.90-0.17 | 8.85-10.5 | 14 | 9.80 | 1.05 | 0.9956 |
| Average | | | | | | 9.80 (4) | 1.05 (2) | |

Log $K_1^e$ = 9.78

For the reaction: $Z^{\pm=} + H^+ \overset{K_1}{\rightleftharpoons} ZH^{\pm=}$

| Monomer 11 | | | | | | | | |
|---|---|---|---|---|---|---|---|---|
| 1 | 0.2912 (11: ZH$_4^+$) | −0.09690 | 0.84-0.16 | 6.75-8.30 | 17 | 7.48 | 1.03 | 0.9935 |
| 3 | 0.2507 (ZH$_4^+$) | −0.09690 | 0.91-0.14 | 6.50-8.20 | 16 | 7.42 | 0.97 | 0.9934 |
| 2 | 0.2102 (ZH$_4^+$) | −0.09690 | 0.93-0.23 | 6.40-7.95 | 14 | 7.41 | 0.94 | 0.9960 |
| Average | | | | | | 7.44 (4) | 0.98 (5) | |

Log $K_2^e$ = 7.43

For the reaction: $ZH^{\pm=} + H^+ \overset{K_2}{\rightleftharpoons} ZH_2^{\pm-}$

| Monomer 11 | | | | | | | | |
|---|---|---|---|---|---|---|---|---|
| 1 | 0.2912 (11: ZH$_4^+$) | −0.09690 | 0.31-0.21 | 2.70-2.93 | 14 | 2.38 | 0.95 | 0.9917 |
| 2 | 0.2507 (ZH$_4^+$) | −0.09690 | 0.27-0.19 | 2.74-2.94 | 10 | 2.34 | 0.96 | 0.9941 |
| 3 | 0.2102 (ZH$_4^+$) | −0.09690 | 0.25-0.16 | 2.80-3.04 | 8 | 2.27 | 1.06 | 0.9795 |
| Average | | | | | | 2.33 (6) | 0.99 (6) | |

Log $K_4^e$ = 2.30

For the reaction: $ZH_3^+ + H^+ \overset{K_4}{\rightleftharpoons} ZH_4^+$ $^a$Titrant concentration (negative values indicate titrations with NaOH),
$^b$Number of data points from titration curve,
$^c$Values in the parentheses are standard deviations in the last digit,
$^d$R = Correlation coefficient.
$^e$log $K_l$ = log $K_l^o$.

Unlike the monomer, the polymer's basicity constant of an anionic motif in a repeating unit depends on the charges on the neighboring units. Log $K_3$ of the monomer cannot be determined for the reason given in the experimental. The basicity constants log $K_1$ and log $K_3$ are of "apparent" (Barbucci, R.; Casolaro, M.; Danzo, N.; Barone, V.; Ferruti, P.; Angeloni, A.; *Macromolecules* 1983, 16, 456—incorporated herein by reference in its entirety) nature (n>1) as demonstrated in FIG. 6 which reveals a decrease in log K with the increase in degree of protonation (α). FIG. 6 is a plot for the apparent log $K_1$, log $K_2$ and log $K_3$ versus degree of protonation (α) (entries 3, 3 and 3, Table III) for (±≡) PZDAN 9. A decrease in log $K_1$ and log $K_3$ of respective $^{2-}O_3P$—$X^+$—$PO_3^{2-}$ (10) and $^-HO_3P$—$X^+$—$PO_3H^-$ (8) [owing to gradual change of (±≡) and (±−) motifs to (±=) (±), respectively], with the increase in α is a direct consequence of a decrease in the corroborated by the viscosity values of 8 in salt-free water (FIG. 5). A polymer concentration of ≈0.05 g/dL is used for the determination of basicity constants in almost salt-free water (0.0175 M NaCl); even though the viscosity value of (±) 7 was not determined owing to solubility problem in salt-free water its viscosity value in collapsed coil conformation is expected to be much lower than that of (±−) 8. Therefore (±) 7 is least hydrated, and the transformation of (±−) 8 to (±) 7 would thus require the release of the greatest number of hydrated water molecules during each step of protonation thereby resulting in the greatest value for the polyelectrolyte index.

Smooth functioning of a desalination process is often plagued by precipitation (scale formation) of $CaCO_3$, $CaSO_4$, $Mg(OH)_2$, etc. Inhibition of growth rate of crystal formation by commonly used anionic antiscalants like poly(phosphate)

s, organophosphates, and polyelectrolytes (Gill, J. S. *Desalination* 1999, 124, 43; David, H.; Hilla, S.; Alexander S. *Ind. Eng. Chem. Res.* 2011, 50, 7601—each incorporated herein by reference in its entirety) is associated with their ability to sequestrate polyvalent cations and alter the crystal morphology at the time of nucleation and inhibit its growth (Davey, R. J. In The Role of Additives in Precipitation Processes, Industrial Crystallization 81, Eds. Jancic, S. J.; de Jong, E. J., Eds.; North-Holland Publishing Co; 1982, 123; Spiegler, K. S.; Laird, A. D. K. Principles of Desalination, Part A, 2nd ed.; Academic Press; New York, 1980—each incorporated herein by reference in its entirety)

Figure 7:
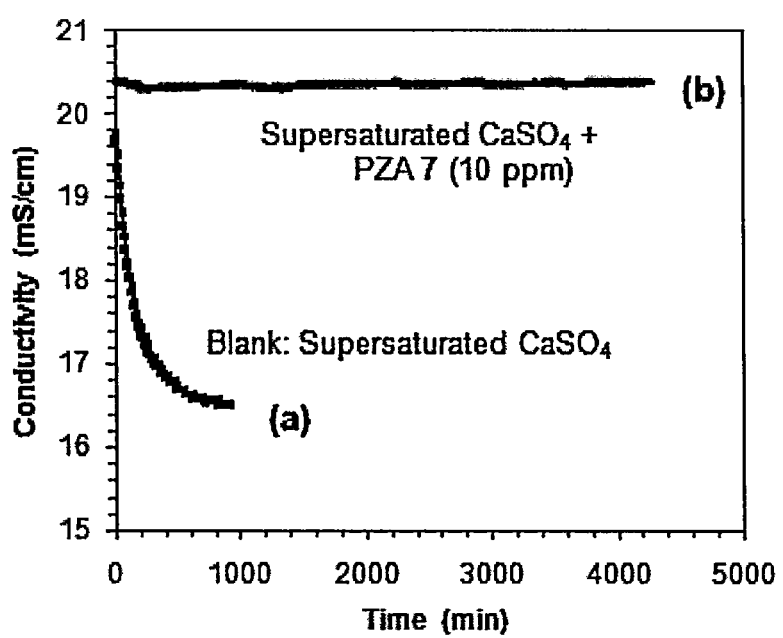
FIG. 7 shows the precipitation behavior of a supersaturated solution in the presence and absence of PZA 7.

The reject brine in the Reverse Osmosis (RO) process contains dissolved salts which precipitate in the event of exceeding their solubility limits. Antiscalant behavior of a supersaturated solution of $CaSO_4$ containing 2600 ppm of $Ca^{2+}$ and 6300 ppm of $SO_4^{2-}$ was investigated using conductivity measurements of 3CB solutions in the absence and presence of in the presence of 10 ppm of PZA 7 (FIG. 7). FIG. 7 shows the precipitation behavior of a supersaturated solution (3CB) of $CaSO_4$ in the presence (10 ppm) and absence of PZA 7. Conductivity did not decrease for about 4280 min (71.3 h) thus registering an amazing ≈100% scale inhibition in the presence of a meager 10 ppm of PZA 7 (FIG. 7b). Note that precipitation started immediately in the absence of antiscalant (FIG. 7a: Blank). The newly developed antiscalant may continue to inhibit precipitation even for longer duration; however the test was abandoned after 71.3 h. It is worth mentioning that the residence time of reject brine in an osmosis chamber of a desalination plant is for duration of ≈30 min only. The optimistic result thus certifies that the additive is very much suitable for use in inhibiting calcium sulfate precipitation in RO plants. It is worth mentioning that neither monomers 4 and 11 nor polymer 5 gave any effective inhibition; since screening experiments based on visual inspection revealed that under the same conditions the system becomes cloudy within 1 h.

The work describes the synthesis and polymerization of a new cationic monomer 4. Polymer CPE 5 represents the first example of a Butler's symmetric cyclopolymer containing two identical phosphopropyl pendents in the same repeating unit. The hydrolysis of the phosphonate ester groups resulted in the pH-responsive CPE (+) 6 which permitted to study the interesting solution properties (including solubility behavior) that involved its conversion to (±−) PZA 7, (±−) PZAN 8, (±=) PZDAN 9, and (±≡) PZTAN 10 all having identical degree of polymerization. The solution properties were correlated to the type of charges and their densities on the polymer chain. Several apparent basicity constants of (=≡) PZTAN 9 and monomer (±≡) ZTAN 15 have been determined. PZA 7 at a meager concentration 10 ppm imparted excellent inhibition of the formation of calcium sulfate scale and as such it can be used effectively as an antiscalant additive in Reverse Osmosis plant.

A new symmetrically substituted cationic monomer bis[3-(diethoxyphosphoryl)propyl]diallylammonium chloride was synthesized and cyclopolymerized to give the corresponding cationic polyelectrolyte (CPE) (+) bearing two identical (diethoxyphosphoryl)propyl penedents on the pyrrolidinium repeating units. The hydrolysis of the phosphonate ester in (CPE) (+) gave a pH-responsive cationic polyacid (CPA) (+) bearing the motifs of a tetrabasic acid. The (CPA) (+) under pH-induced transformation was converted into a water-insoluble polyzwitterion acid (±) (PZA) or water-soluble polyzwitterion/anion (±−) (PZAN) or polyzwitterion/dianion (±=) (PZDAN) or polyzwitterion/trianion (±≡) (PZTAN), all having identical degree of polymerization. The interesting solubility and viscosity behaviors of the polymers have been investigated in some detail. The apparent protonation constants of the anioinic centers in (±≡) (PZTAN) and its corresponding monomer (±≡) (ZTAN) have been determined. Evaluation of antiscaling properties of the PZA using supersaturated solutions of $CaSO_4$ revealed ≈100% scale inhibition efficiency at a meager concentration of 10 ppm for a duration over 71 h at 40° C. The PZA has the potential to be used effectively as an antiscalant in Reverse Osmosis plant.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A symmetrically substituted cationic monomer having the following formula:

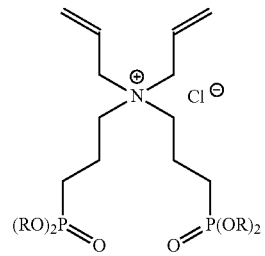

where R is a $C_1$ to $C_6$ alkyl group or a $C_6$-$C_{12}$ aryl group.

2. The cationic monomer of claim 1, wherein the alkyl group R is $CH_2CH_3$.

3. A cationic polyelectrolyte having the following formula:

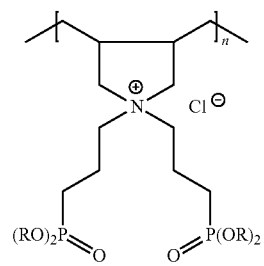

where R is a $C_1$ to $C_6$ alkyl group or a $C_6$-$C_{12}$ aryl group; and where n is an integer of 10 or greater.

4. The cationic polyelectrolyte of claim 3, wherein the alkyl group R is $CH_2CH_3$; and n is the number of repeating units in the range of 20-1,500.

5. A cationic polyacid having the following formula:

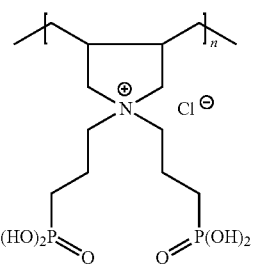

where n is an integer of 10 or greater.

6. The cationic polyacid of claim 5, wherein n is the number of repeating units in the range of 20-1,500.

7. A polyzwitterion acid polymer having the following formula:

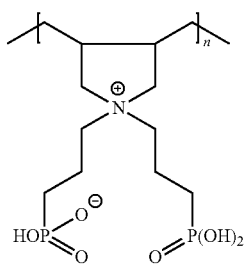

where n is an integer of 10 or greater.

8. The polyzwitterion acid of claim 7, wherein n is the number of repeating units in the range of 20-1,500.

9. A poly(zwitterion/anion) having the following formula:

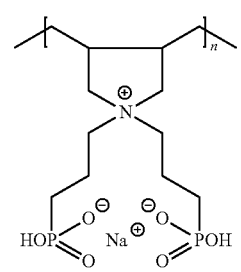

wherein n is an integer of 10 or greater.

10. The poly(zwitterion/anion) of claim 9, wherein n is the number of repeating units in the range of 20-1,500.

11. A poly(zwitterion/dianion) having the following formula:

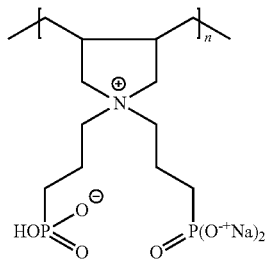

wherein n is an integer of 10 or greater.

12. The poly(zwitterion/dianion) of claim 11, wherein n is the number of repeating units in the range of 20-1,500.

13. A poly(zwitterion/trianion) having the following formula:

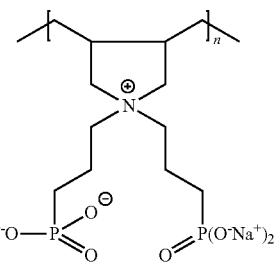

wherein n is an integer of 10 or greater.

14. The poly(zwitterion/trianion) of claim 13 wherein n is the number of repeating units in the range of 20-1,500.

15. A process for antiscaling, comprising:
contacting a composition comprising the polyzwitterion acid polymer of claim 7 with a surface comprising scale to remove the scale from the surface.

* * * * *